United States Patent [19]

Kitahara

[11] 4,087,346

[45] May 2, 1978

[54] ELECTROPHORETIC APPARATUS

[75] Inventor: Tomohiro Kitahara, Hachiouji, Japan

[73] Assignee: Olympus Optical Co., Ltd., Japan

[21] Appl. No.: 695,417

[22] Filed: Jun. 14, 1976

[30] Foreign Application Priority Data

Jun. 14, 1975 Japan .............................. 50-81260[U]
Oct. 14, 1975 Japan ............................ 50-139129[U]
Oct. 14, 1975 Japan ............................ 50-139130[U]

[51] Int. Cl.² ...................... G01N 27/26; G01N 27/28
[52] U.S. Cl. .............................. 204/299 R; 204/180 S;
204/180 G; 204/300 R
[58] Field of Search ..................... 204/299, 300, 180 S,
204/180 G

[56] References Cited

U.S. PATENT DOCUMENTS

| 3,133,009 | 5/1964 | Natelson | 204/299 |
| 3,764,513 | 10/1973 | Saravis | 204/299 |
| 3,896,021 | 7/1975 | Fosslein | 204/299 |

Primary Examiner—Arthur C. Prescott
Attorney, Agent, or Firm—Cushman, Darby & Cushman

[57] ABSTRACT

An electrophoretic apparatus for use in a quantitative analysis of a specimen such as a blood serum applied to a belt-like carrier body, which is capable under the unified conditions of performing the electrophoresis for the blood serum by applying direct voltage to the latter through the carrier body and comprises a main body having a pair of buffer solution troughs respectively containing a buffer solution, a transport means for transporting the carrier body into and out of the main body, a pair of high absorbent paper at least a part of each of which is dipped into the buffer solution in respective buffer solution troughs and contacting means for contacting each side end portion of the carrier body with each one of the high absorbent paper, whereas the direct voltage is applied to the carrier body through the buffer solution and said pair of high absorbent paper.

9 Claims, 13 Drawing Figures

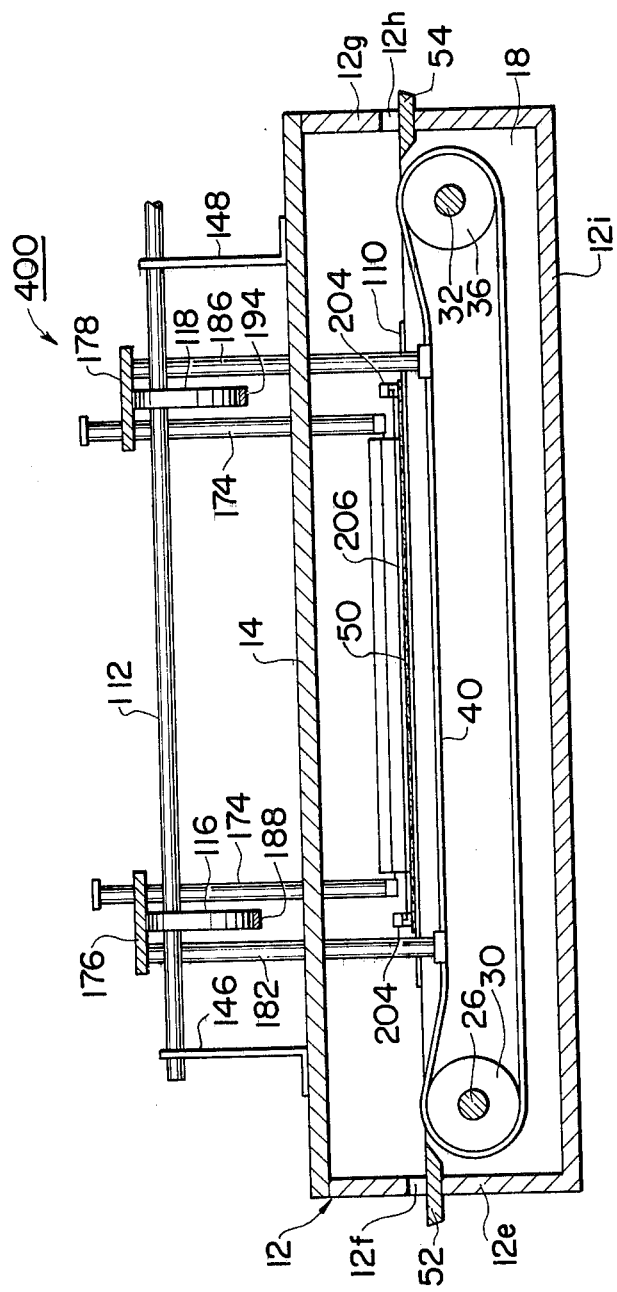

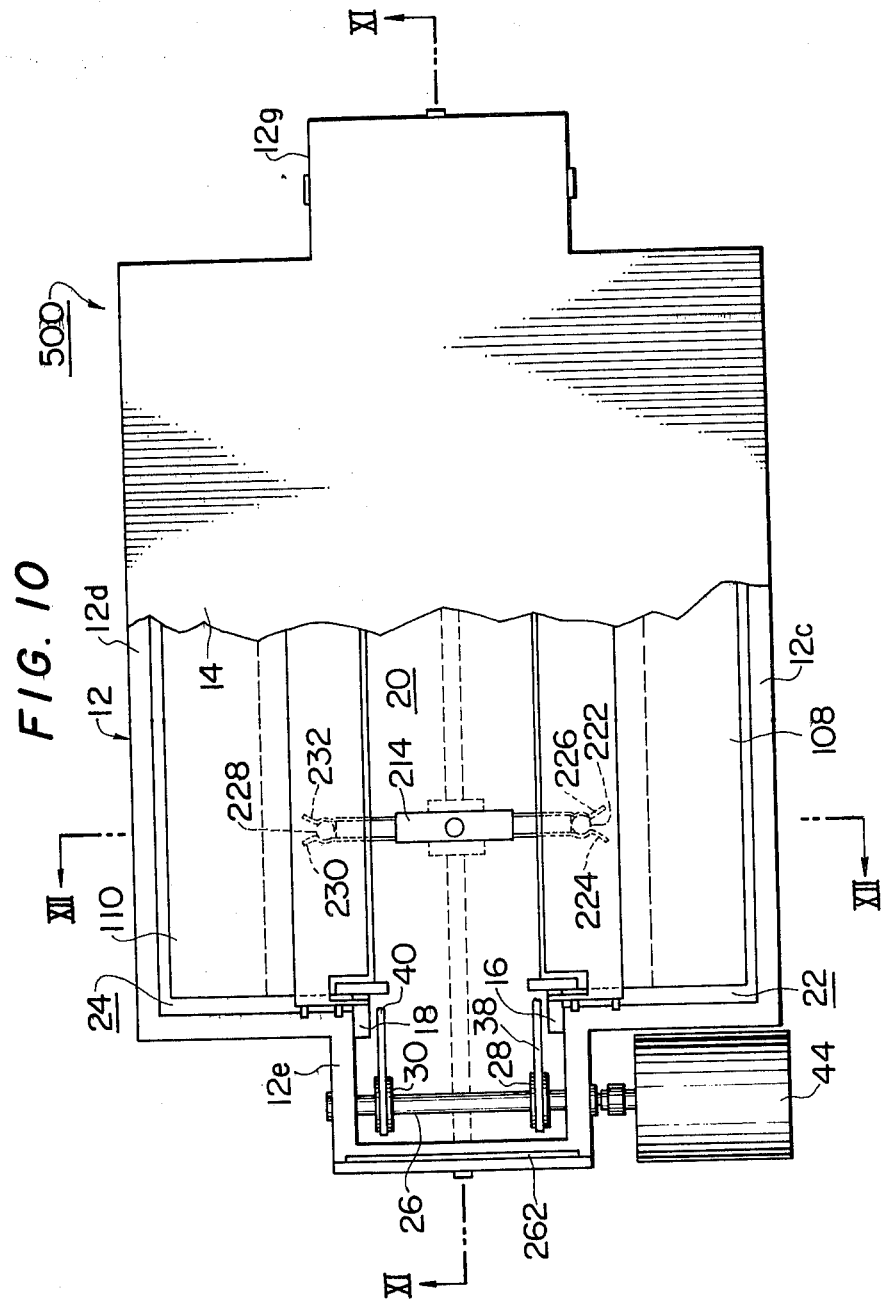

ELECTROPHORETIC APPARATUS

BACKGROUND OF THE INVENTION a. Field of the Invention

The present invention relates generally to an electrophoretic apparatus for use in a quantitative analysis of the blood serum, and more particularly to such apparatus for surely performing, under the unified conditions, the electrophoresis for the blood serum applied to a carrier body which consists of, for example, a sheet of cellulose acetate paper of belt-like form.

b. Description of the Prior Art

In the electrophoretic method for analyzing a blood serum i.e. for measuring quantities of different types of proteins in the blood serum, the blood serum is applied to a carrier body which usually consists of a sheet of cellulose acetate paper of belt-like form and then the blood serum is fractionated into different components of the proteins by means of electrophoresis by applying high direct voltage to the blood serum applied to the carrier body. Therefore, when performing the electrophoresis for the blood serum applied to the carrier body, the carrier body must be correctly set in place within the electrophoretic apparatus. However, almost of all necessary works for the electrophoresis heretofore depend on well-experienced and skillful technician's handwork and this makes it impossible to increase the efficiency of such necessary works for electrophoresis. In addition to this disadvantage, in the electrophoretic apparatus heretofore known in the art the electrical connections between both side ends of the carrier body and electric terminals are often unreliable and thus the measurement accuracy is unfavourably influenced by such unreliable electrical connections.

SUMMARY OF THE INVENTION

It is therefore a primary object of the present invention to provide a novel electrophoretic apparatus capable of increasing the efficiency of the necessary works for the electrophoresis and of successively processing in generally automatic manner a plurality of the carrier bodies to which many of different blood serum to be analyzed are applied.

It is a further object of the present invention to provide an electrophoretic apparatus which can perform the electrophoresis for blood serums applied to carrier bodies under the unified conditions so that more precise or correct results of analysis may be obtained.

It is a still further object of the present invention to provide an electrophoretic apparatus which is simple in its construction and compact in its volume.

BRIEF DESCRIPTION OF THE DRAWINGS

Other objects and features of the invention will become apparent to those skilled in the art as the disclosure made in the following description of preferred embodiments of the invention, as illustrated in the accompanying sheets of drawings, in which like reference numerals or characters designate the same parts throughout the figures and wherein, FIG. 8 shows a sectional front elevational view of the third embodiment of the electrophoretic apparatus according to the present invention, FIG. 10 shows a partially sectioned top plan view of the fourth embodiment of the electrophoretic apparatus according to the present invention.

DESCRIPTION OF THE PREFERRED EMBODIMENTS

Figure 1:
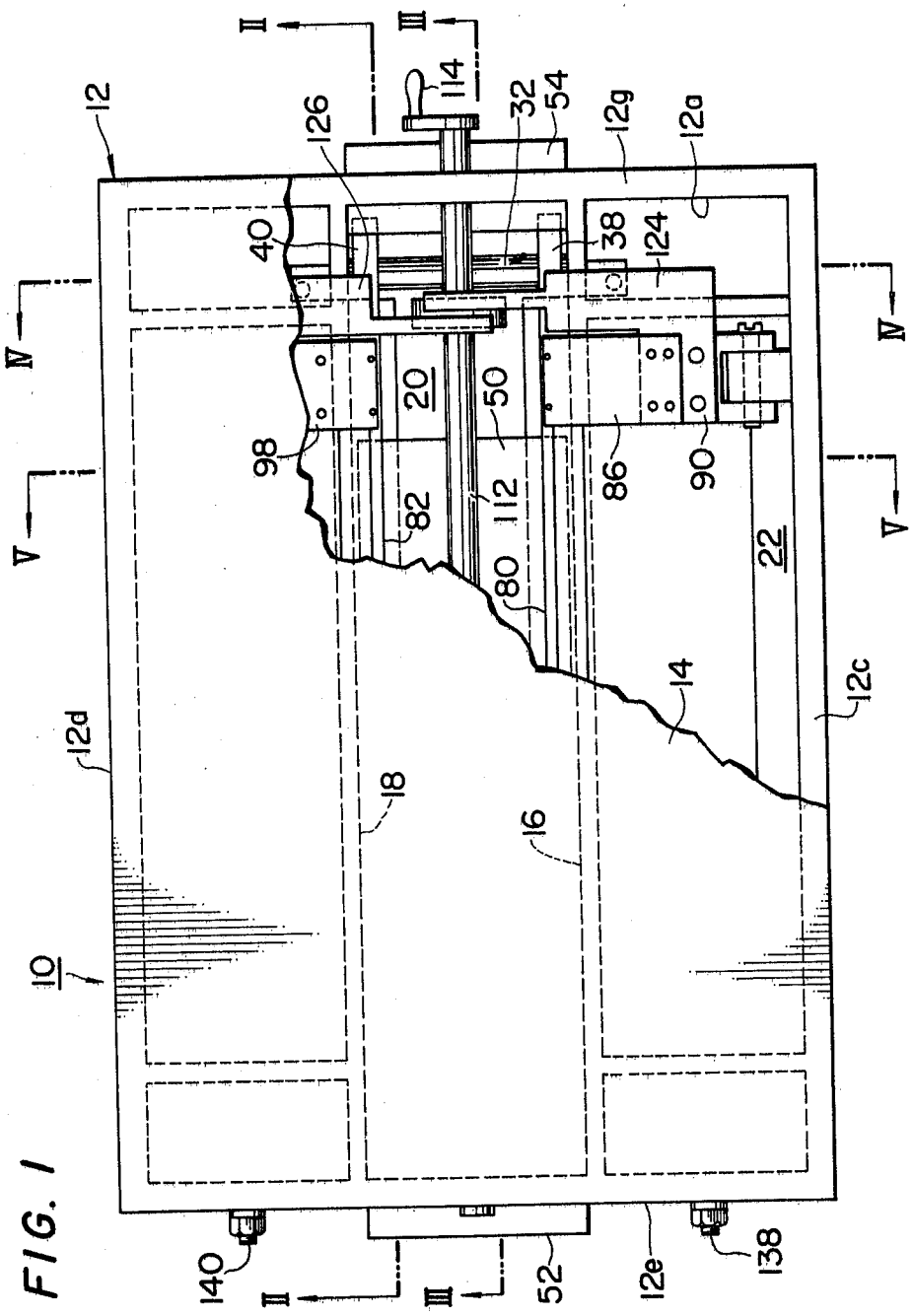
FIG. 1 shows a partially sectioned top plan view of the first embodiment of an electrophoretic apparatus according to the present invention.

Referring now to FIGS. 1 through 5, there is shown a basic electrophoretic apparatus 10 according to the present invention, which comprises a main body 12 having an open topped chamber portion 12a of a rectangular shape and a pair of leg portions 12b. The chamber portion 12a consists of a front wall 12c, a rear wall 12d, a left side wall 12e with a horizontally elongated window 12f, a right side wall 12g with a window 12h similar to the window 12f and formed in alignment with the window 12f, and a bottom wall 12i with a slot 12j. The chamber portion 12a is closed by a lid 14 and divided by a pair of parallel partition walls 16 and 18 into three portions i.e. a central transport portion 20 and a pair of buffer solution trough portions 22 and 24 positioned at both sides of the transport portion 20. A connecting shaft 26 fixedly supporting a pair of rollers 28 and 30 at its both end portions is rotatably supported by the partition walls 16 and 18 at one end portion of the transport portion 20. Similarly, a connecting shaft 32 fixedly supporting a pair of rollers 34 and 36 at its both end portions is rotatably supported by the partition walls 16 and 18 at the other end of the transport portion 20. A pair of endless belts 38 and 40 are spanned between the rollers 28 and 34, and the rollers 30 and 36. The connecting shaft 32 is provided with a pulley 42 at the middle portion thereof where the pulley 42 is in alignment with the slot 12j. An electric motor 44 is mounted on the lower surface of the bottom wall 12i with a pulley 46 fixed to its drive shaft being in alignment with the slot 12j so that the connecting shaft 32 is driven by the motor 44 through an endless rubber belt 48 spanned between both pulleys 42 and 46 through the slot 12j. Therefore, when the motor 44 rotates in the clockwise direction in FIG. 3 the connecting shaft 32 is driven in the same direction and the upper strands of the endless belts 38 and 40 are advanced in the right-hand direction in FIGS. 1 through 3. At the lower portions of the window 12 is an entrance for a carrier body 50 of a belt-like cellulose acetate paper to which the blood serum is applied and the window 12h as an exit for the carrier body 50, guide means 52 and 54 are respectively provided for smooth introduction and delivery of the carrier body 50 into and out of the main body 12 of the electrophoretic apparatus 10.

A pair of pushing plates 56 and 58 respectively having horizontally bent portions 56a and 58a are movably disposed on the inner surfaces of the partition walls 16 and 18 by means of well-known pin-and-slot engagements of a plurality of headed pins 60 through 66 fixed to each partition wall and a plurality of elongated slots 68 through 74 formed in each pushing plate, so that the pushing plates 56 and 58 can move upwardly and downwardly along the respective inner surfaces of the partition walls 16 and 18. Since the horizontally bent portions 56a and 58a are respectively positioned immediately below the upper strands of the endless belts 38 and 40, these upper strands may be pushed upwardly by the corresponding horizontally bent portions 56a and 58a when the pushing plates 56 and 58 are moved in the upward direction along the partition walls 16 and 18. In fact, the respective pushing plates 56 and 58 are continuously biased upwardly by leaf springs 76 and 78 disposed between each of the plates 56 and 58 and each of the partition walls 16 and 18.

A pair of pressing plates 80 and 82 respectively having horizontally bent portions 80a and 82a at their lower ends are disposed above the upper strands of the endless belts 38 and 40 so that each of the horizontally bent portions 80a and 82a is in parallel and superposed relation with respect to each of the horizontally bent portions 56a and 58a of the pushing plates 56 and 58. The pressing plate 80 is connected through a pair of leaf springs 84 and 86 to a pair of rotatable members 88 and 90 which are rotatably supported on the front wall 12c with bolts 92 and 94 being as rotational axes. Similarly, the pressing plate 82 is connected through another pair of leaf springs 96 and 98 to a pair of rotatable members 100 and 102 which are supported on the rear wall 12d with bolts 104 and 106 being as rotational axes. Two sheets of high absorbent paper 108 and 110 such as filter paper are respectively attached to the lower surfaces of the horizontally bent portions 80a and 82a of the pressing plates 80 and 82. The greater part of each high absorbent paper is dipped into a buffer solution 111 which is separately contained in the buffer solution troughs 22 and 24.

An operating rod 112 is rotatably supported by the left and right side walls 12e and 12g of the main body 12 so that it extends above the longitudinal center line of the transport portion 20. A handle 114 is fixed at one end of the operating rod 112, which extends outwardly through the right side wall 12g of the main body 12. The operating rod 112 is provided with a pair of cam disks 116 and 118. A pair of rigid arms 120 and 122 are respectively fixed to the rotatable members 88 and 100 so that their free ends are engageable with the periphery of the cam disk 116. Similarly, a pair of rigid arms 124 and 126 are respectively fixed to the rotatable members 90 and 102 so that their free ends are engageable with the periphery of the cam disk 118. In FIGS. 1 through 5, the free ends of the arms 120 through 126 are in the lowermost position where the horizontally bent portions 80a and 82a of the pressing plates 80 and 82 can lightly press the belts 38 and 40 through the high absorbent paper 108 and 110 against the horizontally bent portions 56a and 58a of the pushing plates 56 and 58. The free ends of the arms 120 through 126 are moved upwardly as the cam disks 116 and 118 are rotated together with the operating rod 112 from the positions shown in FIGS. 1 through 5 by means of the handle 114. Therefore, when the cam disks 116 and 118 are rotated at 180° from the positions shown in FIGS. 1 through 5, there are formed sufficient air spaces between the upper strands of the belts 38 and 40 and the absorbent paper 108 and 110 attached to the horizontally bent portions 80a and 82a to allow the passing of the carrier body 50.

The rigid arms 120 through 126 are respectively provided with connecting members 128 through 134. Each of the connecting members 128 through 134 is pivotably supported at its one end to the corresponding rigid arm so as to extend downwardly by the gravity. A plate member 136 having an uprightly extending portion 136a for preventing the carrier body 50 from slackening is suspended by the four connecting members 128 through 134 so that the plate member 136 can move vertically in accordance with the rotation of the cam disks 116 and 118 and that the ridge of the uprightly extending portion will be in a plane including top surfaces of the upper strands of the endless belts 38 and 40 when the free ends of the rigid arms 120 through 126 are brought into their uppermost positions.

A pair of terminals 138 and 140 to be connected to an electric power supply (not shown) are mounted to the left side wall 12e of the main body 12, so that the direct voltage for electrophoresis is applied to the buffer solution 111 through, for example, a pair of platinum wires (not shown) respectively connected to the terminals 138 and 140 with their free ends dipped into the buffer solution 111 in respective troughs 22 and 24.

In this electrophoretic apparatus 10, since two sheets of high absorbent paper 108 and 110 are employed as electric conductors, the parts such as the endless belts 38 and 40, rollers 28, 30, 34 and 36 and the connecting shafts 26 and 32 which have a possibility to short-circuit both of the absorbent paper 108 and 110 are made of non-conductive materials.

The electrophoresis for the blood serum which is applied to the carrier body 50 is performed as follows by employing the electrophoretic apparatus 10 according to the present invention.

Figure 2:
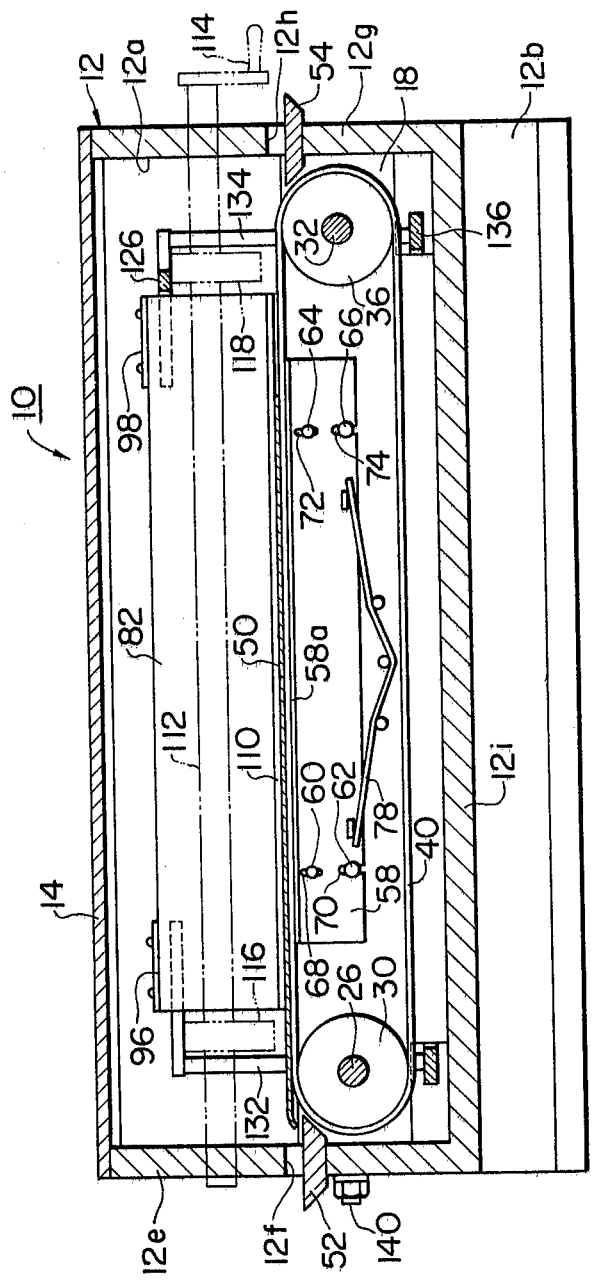
FIG. 2 shows a sectional front elevational view taken along the line II—II of FIG. 1.
Figure 3:
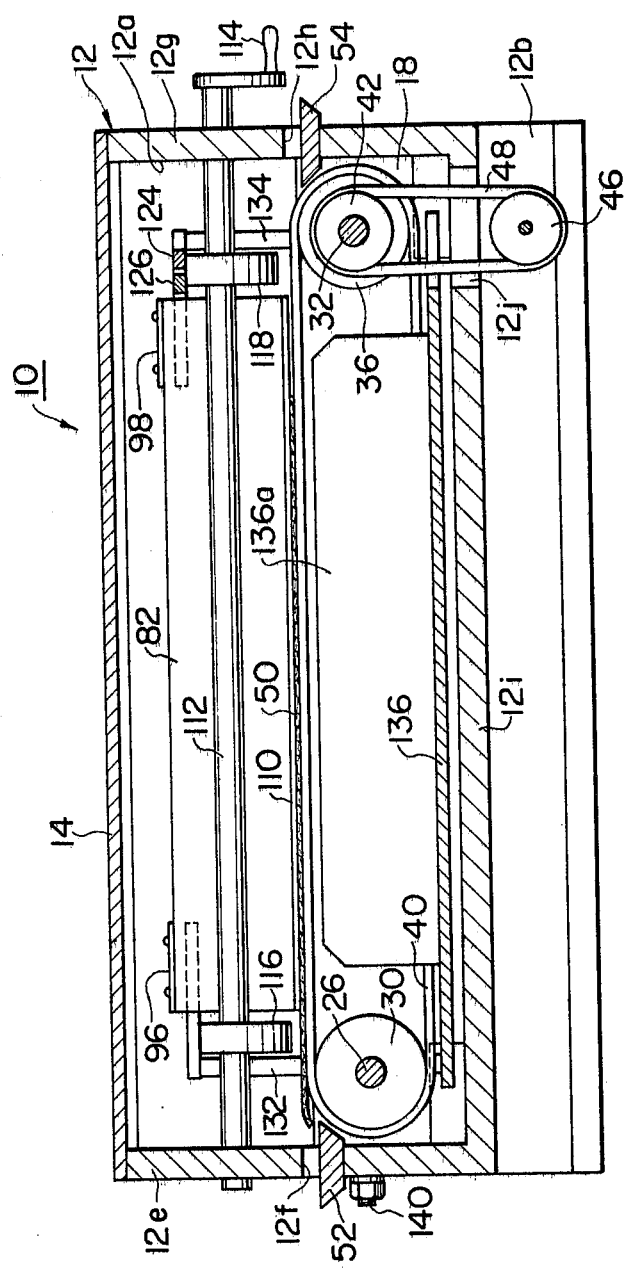
FIG. 3 shows a sectional front elevational view taken along the line III—III of FIG. 1.
Figure 4:
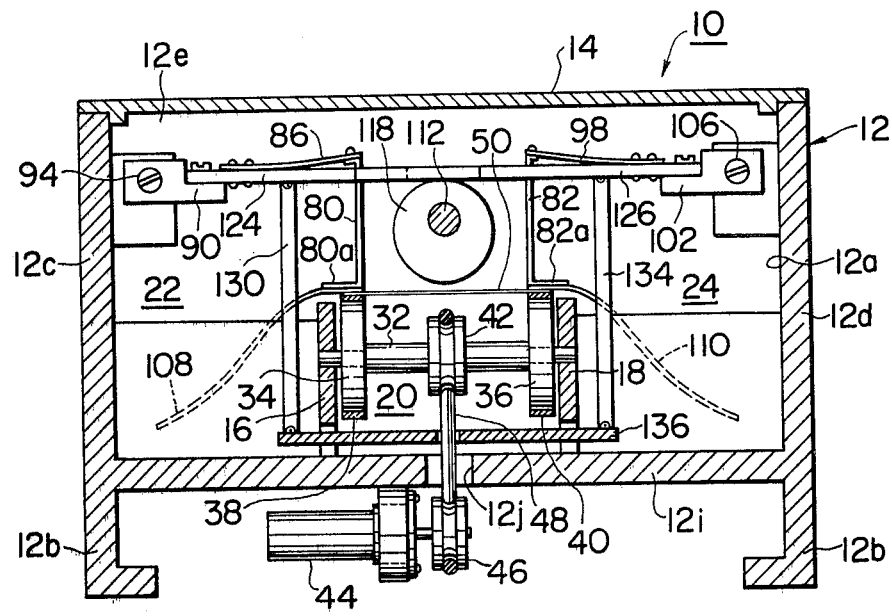
FIG. 4 shows a sectional side elevational view taken along the line IV—IV of FIG. 1.
Figure 5:
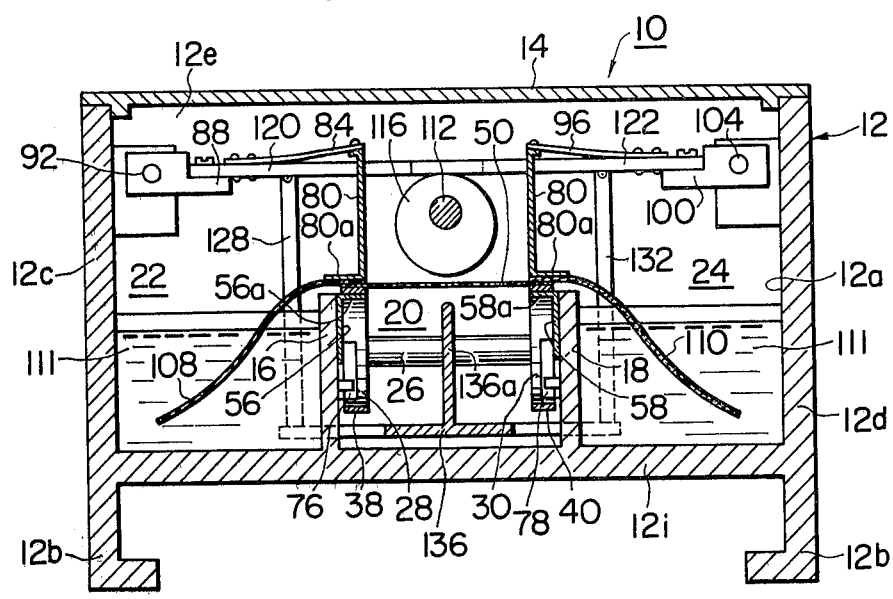
FIG. 5 shows a sectional side elevational view taken along the line V—V of FIG. 1.

Before introducing the carrier body 50 into the electrophoretic apparatus 10, it is necessary to maintain the pressing plate 80 and 82 to be their uppermost positions by rotating the cam disks 116 and 118 at 180° from the positions shown in FIGS. 1 through 5 and to start the motor 44 in order to move the upper strands of the endless belts 38 and 40 in the rightward direction in FIGS. 1 through 3. The carrier body 50 is introduced into the main body 12 through the entrance window 12f by a suitable transport mechanism (not shown). When the front end portion of the carrier body engages with the endless belts 38 and 40, the carrier body 50 is dragged on the upper strands of the endless belts 38 and 40 due to the friction therebetween and advanced together with the belts 38 and 40 in the rightward direction in FIGS. 1 through 3 with its both side end portions riding on the upper strands of the belts 38 and 40. The motor 44 is then stopped when the front end portion of the carrier body 50 has arrived at the position below the cam disk 118, so that the carrier body 50 is set in place within the electrophoretic apparatus 10. Since the pressing plates 80 and 82 are in their uppermost positions and the ridge of the uprightly extending portion 136a of the plate member 136 is in a plane including top surfaces of the upper strands of the belts 38 and 40 during the transport of the carrier body 50, the carrier body 50 is smoothly transported without any slackening. Therefore, the carrier body 50 is sustained horizontally when it is set in place within the main body 12. Then the cam disks 116 and 118 are rotated at 180° by manually operating the handle 114. The free ends of the rigid arms 120 through 126 move from their uppermost positions toward their lowermost positions following the rotation of the cam disks 116 and 118, and finally arrive at their lowermost positions where the horizontally bent portions 80a and 82a of the pressing plates 80 and 82 press the high absorbent paper 108 and 110 against the both side end portions of the carrier body 50. The carrier body 50 sustained horizontally by means of the ridge of the uprightly extending portion 136a of the plate member 136 is thus held firmly in place without slackening, though the ridge of the uprightly extending portion 136a moves below the carrier body 50 together with the downward movement of the pressing plates 80 and 82. Then, the direct voltage is applied for a predetermined period of time to the blood serum applied on the carrier body 50 which is held in place within the main body 12 and the electrophoresis for the blood serum is performed. In this case, constant electric current flows from, for example, the terminal 138 via the platinum wire (not shown), the buffer solution 111 in the trough 22, the absorbent paper 108, the carrier body 50, the absorbent paper 110, the buffer solution 111 in the trough 24 and the platinum wire (not shown) to the terminal 140.

After the completion of the electrophoresis for the blood serum applied on the carrier body 50, the carrier body is transported out of the main body 12 through the exit window 12h of the right side wall 12g by lifting up the pressing plates 80 and 82 by means of the operation of the cam disks 116 and 118 and by starting the motor 44 again. The carrier body fed out from the electrophoretic apparatus 10 is then set in a densitometer or filter photoelectric colorimeter for the purpose of quantitative analysis of the blood serum.

Though the operations of the cam disks 116 and 118 and motor 44 are manually controlled in this embodiments, it is easily possible to automate almost of all operations of the electrophoretic apparatus 10 according to the present invention with a sequence control circuit which can sequentially control the movements of the cam disks 16 and 118 and the start and stop of the motor 44.

Figure 6:
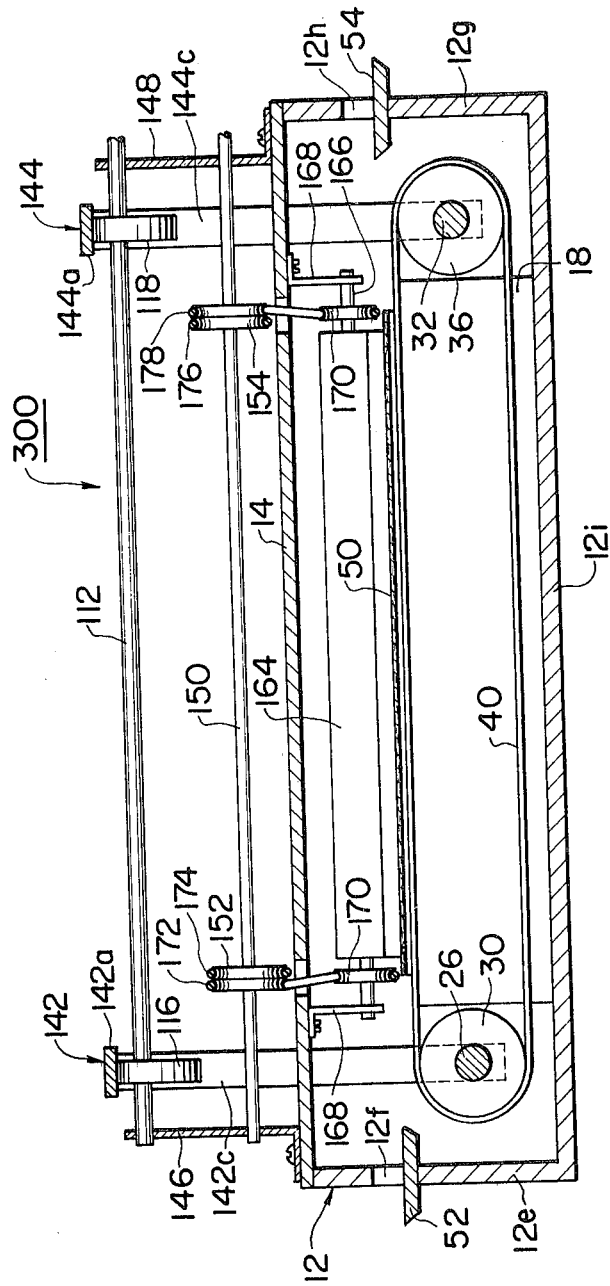
FIG. 6 shows a sectional front elevational view of the second embodiment of the electrophoretic apparatus according to the present invention.
Figure 7:
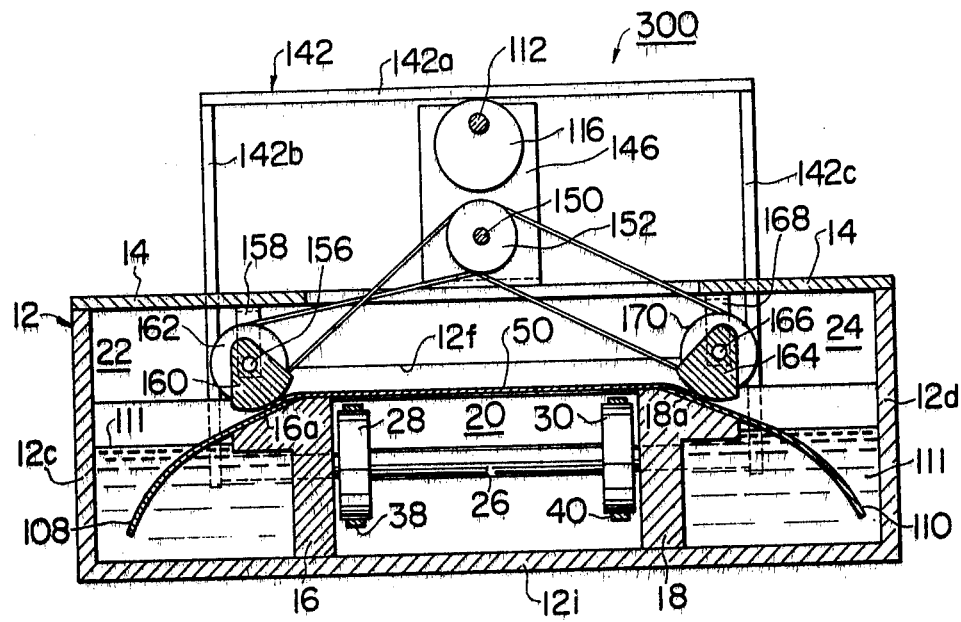
FIG. 7 shows a sectional side elevational view of the electrophoretic apparatus shown in FIG. 6.

In FIGS. 6 and 7, there is shown another embodiment of the electrophoretic apparatus 300 according to the present invention, in which the endless belts 38 and 40 for transporting the carrier body 50 are disengaged from the carrier body 50 whiile the direct voltage is applied to the carrier body 50 in order to avoid possible bad influence by the belts 38 and 40 to the electrophoretic effect. In this embodiment, the partition walls 16 and 18 are respectively provided with slant portions 16a and 18a to which the sheets of high absorbent paper 108 and 110 to be dipped into the buffer solution 111 are respectively attached. A movable frame member 142 consisting of a horizontal bar 142a and a pair of leg portions 142b and 142c which extend downwardly from both ends of the bar 142a is disposed at the left of the main body 12 so that the horizontal bar 142a ridges on the periphery of the cam disk 116 and that the leg portions 142b and 142c extends through slots of the lid 14 into the main body 12. The connecting shaft 26 to which a pair of the rollers 28 and 30 are fixed is rotatably supported by the leg portions 142b and 142c of the frame member 142 at their lower end portions. Another frame member 144 of the same construction as the frame member 142 is similarly disposed at the right portion of the main body 12 in order to rotatably support the connecting shaft 32 to which a pair of the rollers 34 (not shown) and 36 are fixed. Therefore, two pair of the rollers 28, 30, 34 and 36 are moved upwardly and downwardly following the rotation of the cam disks 116 and 118. By means of these movable frame members 142, the upper strands of the endless belts 38 and 40 which are spanned between the rollers 28 and 34 and the rollers 30 and 36 are positioned below a plane including both top surfaces of the partition walls 16 and 18 when the frame members 142 and 144 are their lowermost positions. On the contrary, the upper strands of the belts 38 and 40 are positioned above the plane when the frame member 142 and 144 are their uppermost positions.

A pair of support members 146 and 148 rotatably supporting the operating rod 112 to which the cam disks 116 and 118 are fixed also rotatably supports another operating rod 150 to which a pair of pair-pulleys 152 and 154 are fixed.

Above and along the slant position 16a of the partition wall 16, an operating shaft 156 is rotatably supported by a pair of support members 158 fixed to the right and left portions of the inner surface of the lid 14. A bar-like pressing member 160 of generally sector shape in section is fixed to the operating shaft 156 so that its arcuate surface can press one side end portion of the carrier body 50 introduced into the main body 12, together with the absorbent paper 108 against the slant portion 16a of the partition wall 16. A pair of pulleys 162 are fixed to the operating shaft 156 at the positions adjacent to both ends of the pressing member 160. Another bar-like pressing member 164 of the same construction as one indicated at 160 is similarly disposed above and along the slant portion 18a of the partition wall 18 through an operating shaft 166 by means of a pair of support members 168. A pair of pulleys 170 are also fixed to the operating shaft 166 at the positions adjacent to both ends of the pressing member 164. Drive belts 172 and 174 are respectively spanned between the pair-pulley 152 and each one of the pulleys 162 and 170. Similarly, drive belts 176 and 178 are respectively spanned between the other pair-pulley 154 and each other one of the pulleys 162 and 170.

Though there are not shown in FIGS. 6 and 7, each right end portion of the operating rods 112 and 150 is connected to suitable manipulating means such as a handle similar to one in the first embodiment of the present invention, which is shown in FIGS. 1 through 3 at 114, and the connecting shaft 32 or 26 is coupled to a suitable drive means such as an electric motor in the same manner as in the case of the first embodiment.

Before introducing the carrier body 50 into the main body 12 of the electrophoretic apparatus 10, the rollers 28, 30, 34 (not shown), and 36 are set in their uppermost positions by rotating the cam disks 116 and 118, and the pressing members 160 and 164 are rotated in the positions where their arcuate surfaces may be opposite to the lower surface of the lid 14 so as not to obstruct the transport of the carrier body 50. The pressing members 160 and 164 are simultaneously rotated through a pair of the pair-pulleys 152 and 154, the drive belts 172 through 178 and two pairs of pulleys 162 and 170 when the operating rod 150 is rotated.

The carrier body 50 introduced into the main body 12 through the entrance window 12f is advanced together with the belts 38 and 40 in the rightward direction in FIG. 6 with its both side end portions which extends outwardly from the belts 38 and 40 being downwardly bent by the gravity. The motor (not shown) for driving the endless belts 38 and 40 is then stopped when the carrier body 50 has arrived at the position shown in FIG. 6. In this condition, the operating rod 150 is rotated in the counterclockwise direction until the arcuate surfaces of the pressing members 160 and 164 press the both side end portions of the carrier body 50 against the high absorbent paper 108 and 110 on the slant portions 16a and 18a of the partition walls 16 and 18. Since the pressing member 160 is rotated in the clockwise direction and the pressing member 164 is rotated in the counterclockwise direction so as to outwardly stretch the both side end portions of the carrier body due to the friction therebetween, the carrier body 50 is held in place with its slack completely removed. Then the cam disks 116 and 118 are rotated by the operating rod 112 so that the connecting shafts 26 and 32 are lowered together with the rollers 28, 30, 34 (not shown) and 36 and the upper strands of the endless belts 38 and 40 is disengaged from the carrier body 50, as shown in FIGS. 6 and 7.

After the carrier body 50 is set in place with its both side ends tightly engaged with each of the high absorbent paper 108 and 110, direct voltage is applied to the both side ends of the carrier body to perform electrophoresis for the blood serum applied to the carrier body in the same manner as in the case of the first embodiment shown in FIGS. 1 through 5. In this second embodiment of the present invention, more precise results of analysis than the results obtained by the apparatus shown in FIGS. 1 through 5 will be obtained, since the endless belts 38 and 40 which possibly exert a bad influence to the results of analysis are completely disengaged from the carrier body 50 during the period of the electrophoresis.

Figure 9:
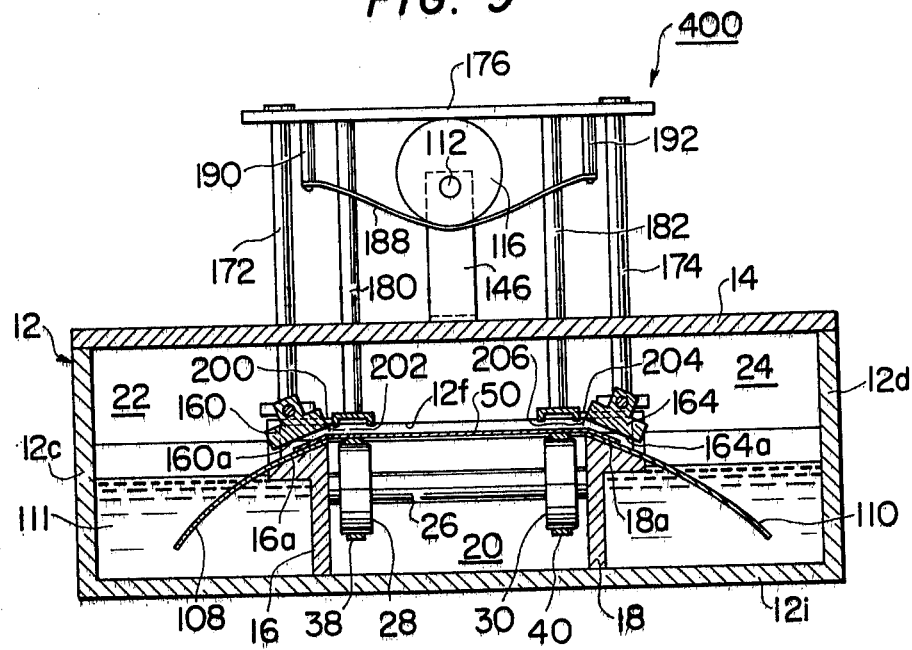
FIG. 9 shows a sectional side elevational view of the electrophoretic apparatus shown in FIG. 8.

In FIGS. 8 and 9, there is shown a still another embodiment of the electrophoretic apparatus 400 according to the present inveniton, in which the endless belts 38 and 40 for transporting the carrier body 50 are disengaged from the carrier body 50 while the direct voltage is applied to the carrier body 50, as in the second embodiment of the present invention shown in FIGS. 6 and 7. As shown in FIGS. 8 and 9, the pressing members 160 and 164 for pressing the both side end portions of the carrier body 50 against the high absorbent paper 108 and 110 attached on the slant positions 16a and 18a of the partition walls 16 and 18 provide flat surfaces 160a and 164a and are supported with their flat surfaces 160a and 164a being in parallel with the slant portions 16a and 18a by two pairs of headed rods 172 and 174 which are movable through each one of a pair of horizontal support plates 176 and 178 and the lid 14. The horizontal support plates 176 and 178 are respectively supported by the cam disks 116 and 118 with their lower surfaces engaged with the top peripheries of the cam disks 116 and 118 so as to move vertically following the rotation of the cam disks 116 and 118. The cam disks 116 and 118 are in their lowermost positions in FIG. 8 and in their uppermost positions in FIG. 9. A pair of pressing rods 180 and 182 are fixed to the horizontal support plate 176 so that they extend downwardly above the left portions of the upper strands of the endless belts 38 and 40. Another pair of pressing rods 184 (not shown) and 186 are similarly fixed to the horizontal support plate 178 so that they extend downwardly above the right positions of the upper strands of the endless belts 38 and 40. The lower end of each pressing rod is positioned above the upper strands of the endless belts 38 and 40 as shown in FIG. 9 when the horizontal support plates 176 and 178 are in their uppermost positions. When the horizontal support plates 176 and 178 are moved in their lowermost positions, the lower ends of the pressing rods 180 through 186 press the upper strands of the endless belts 38 and 40 downwardly so that the upper strands of the belts 38 and 40 are positioned sufficiently below their normal positions, as shown in FIG. 8. In order to ensure the downward movement of the horizontal support plate 176, a steel belt 188 spanned between a pair of studs 190 and 192 which are downwardly fixed to the horizontal support plate 176 is engaged with the lower periphery of the cam disk 116. Similarly, another steel belt 194 spanned between a pair of studs (not shown) which are downwardly fixed to the horizontal support plate 178 is engaged with the lower periphery of the cam disk 118 for the purpose of ensuring the downward movement of the horizontal support plate 178. A pair of inverted L-shaped support members 200 are respectively fixed to the partition wall 16 at the positions adjacent to a pair of the headed rods 172 so as to hold a steel wire 202 therebetween. Another pair of inverted L-shaped support members 204 are similarly disposed to the partition wall 18 at the positions adjacent to a pair of the headed rods 174 so as to hold another steel wire 206 therebetween.

In operation, the horizontal support plates 176 and 178, the headed rods 172 and 174 and the pressing rods 180 through 186 are set in their uppermost positions shown in FIG. 9 by rotating the cam disks 116 and 118 by means of the operating means (not shown) connected to the right end portion of the operating rod 112, before the carrier body 50 is introduced into the main body 12 of the electrophoretic apparatus 400. Thus, the upper strands of the endless belts 38 and 40 are advanced in their normal paths in the rightward direction in FIG. 1 when the connecting shaft 26 or 32 is rotated in the clockwise direction by the drive means (not shown), and sufficient air spaces to allow the passing of the carrier body 50 are formed between the lower surfaces 160a and 164a of the pressing members 160 and 164 and the respective high absorbent paper 108 and 110 attached on the slant portions 16a and 18a of the partition walls 16 and 18.

The carrier body 50 introduced into the main body 12 through the entrance window 12f is advanced together with the upper strands of the endless belts 38 and 40 in the rightward direction in FIG. 8 with its both side end portions being downwardly bent by the gravity. The drive means or the motor (not shown) for driving the endless belts 38 and 40 is then stopped when the carrier body 50 has arrived at the position shown in FIG. 8. In this condition, the operating rod 112 and the cam disks 116 and 118 are rotated at 180° from the positions shown in FIG. 9 so that the horizontal support plates 176 and 178 are moved downwardly to their lowermost positions shown in FIG. 8. Therefore, the both side end portions of the carrier body 50 are respectively pressed by the lower surfaces of the pressing members 160 and 164 against the high absorbent paper 108 and 110 attached on the slant portions 16a and 18a of the partition walls 16 and 18, and simultaneously the upper strands of the endless belts 38 and 40 are pressed downwardly by the pressing rod 180 through 186 and disengaged from the carrier body 50 as shown in FIG. 8. Direct voltage is then applied for the predetermined periods of time through the buffer solution in the buffer solution troughs 22 and 24 and the high absorbent paper 108 and 110 to the carrier body 50 i.e. the blood serum applied thereto. After the completion of the electrophoresis for the blood serum applied to the carrier body 50, the horizontal support plates 176 and 178 are returned by the cam disks 116 and 118 to its uppermost positions shown in FIG. 9 together with the pressing rods and the headed rods and then the carrier body is fed out from the exit window 12h by the upper strands of the endless belts 38 and 40. Even though the both side end portions of the carrier body 50 are adhered to the lower surfaces of the pressing members 160 and 164 due to the viscosity of the buffer solution contained in the carrier body 50 when the pressing members 160 and 164 return from their lowermost positions to their uppermost positions, the carrier body 50 is torn off from the lower surfaces of the pressing member 160 and 164 by the wires 202 and 206. In this third embodiment of the present invention, the same precise results of analysis as in the case of the second embodiment shown in FIGS. 6 and 7 will also be obtained, since the endless belts 38 and 40 are disengaged from the carrier body while the direct voltage is applied to the carrier body 50.

Figure 11:
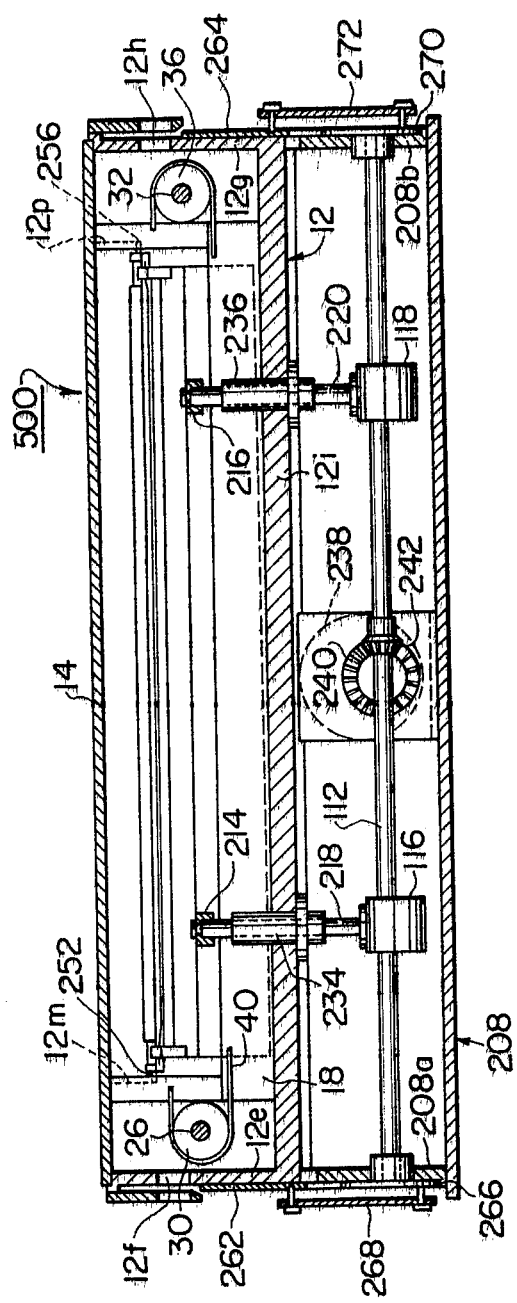
FIG. 11 shows a sectional front elevational view taken along the line XI—XI of FIG. 10.
Figure 12:
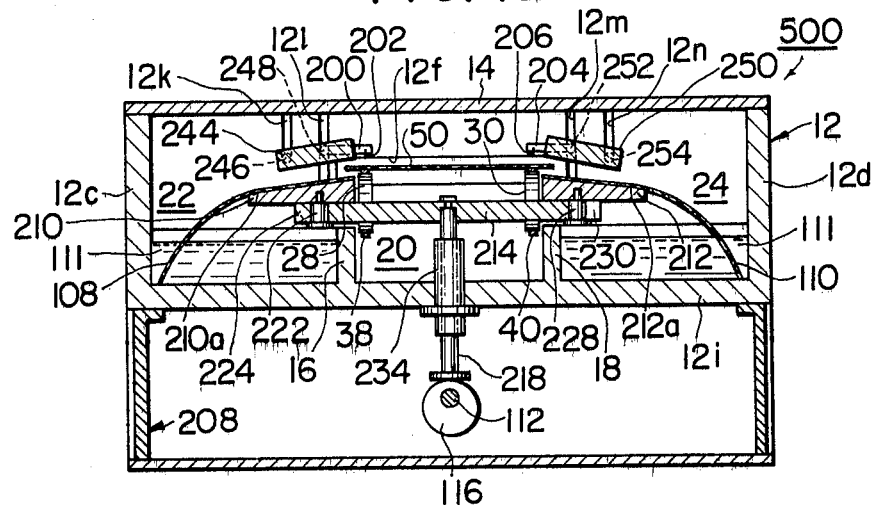
FIG. 12 shows a sectional side elevational view taken along the line XII—XII of FIG. 10.

Still another embodiment of the electrophoretic apparatus 500 according to the present invention is shown in FIGS. 10 through 12, in which the endless belts 38 and 40 for transporting the carrier body 50 are disengaged from the carrier body 50 and both the entrance window 12f and the exit window 12h are shut while the direct voltage is applied to the carrier body 50. In this embodiment, the main body 12 is supported by a support casing 208 having left and right side walls 208a and 208b the outer surfaces of which are respectively flush with the outer surfaces of the left and right side walls 12e and 12g of the main body 12. The sheets of high absorbent paper 108 and 110 are respectively attached on slant surfaces 210a and 212a of a pair of narrow boards 210 and 212 which are symmetrically disposed at both sides of the transport portion 20 of the main body 12. The boards 210 and 212 are connected to each other by a pair of connecting bars 214 and 216 which are further connected to a pair of vertically movable rods 218 and 220. The lower ends of the vertically movable rods 218 and 220 are engaged with the top peripheries of the cam disks 116 and 118 fixed to the operating rod 112 which is rotatably supported by the left and right side walls 208a and 208b of the support casing 208. Therefore, the pair of boards 210 and 212 are moved together in the vertical direction in accordance with the rotation of the cam disks 116 and 118. The board 210 is connected to the connecting bar 214 by inserting a pin 222 fixed to the lower horizontal surface of the board 210 into a pair of leaf springs 224 and 226 fixed to one end of the connecting bar 214. The board 212 is similarly connected to the connecting bar 214 by inserting a pin 228 fixed to the board 212 into a pair of leaf springs 230 and 232 fixed to the other end of the connecting bar 214. The connecting bar 216 is connected to the boards 210 and 212 in the same way as the connecting bar 214. A pair of guide sleeves 234 and 236 are fixed to the bottom wall 12i of the main body 12 so as to smoothly guide the rods 218 and 220 in the vertical direction.

The operating rod 112 is rotated by an electric motor 238 as shown in FIG. 11 through a first bevel gear 240 fixed to a drive shaft of the motor 238 and a second bevel gear 242 fixed to the middle portion of the operating rod 112.

A pressing board 224 is disposed above and along the board 210 with a pair of pins 246 and 248 fixed to the left side end thereof and another pair of pins (not shown) fixed to the right side end thereof being inserted in a pair of elongated slots 12k and 12l formed in the left side wall 12e and another pair of elongated slots (not shown) formed in the right side wall 12g of the main body 12. Similarly, another pressing board 250 of the same construction as the pressing board 244 is disposed above and along the board 212 as in the same manner as the pressing board 244. In FIGS. 10 through 12, reference numerals 252 through 256 respectively represent pins fixed to the pressing board 250 and reference numerals 12m, 12n and 12p respectively represent elongated slots formed in the left and right side walls 12e and 12g of the main body 12 so that they receive the respective pins 252 through 256. A pair of the pressing board 244 and 250 are usually in the lowermost positions in FIGS. 11 and 12 by the gravity, where the lower surfaces thereof are slightly above the upper strands of the endless belts 38 and 40.

Figure 13:
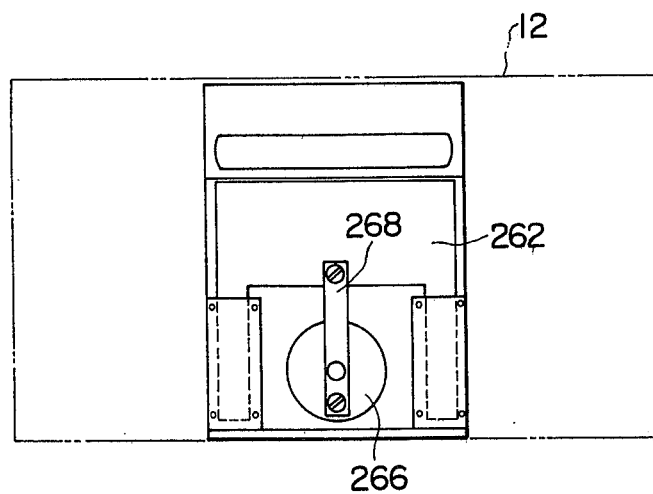
FIG. 13 shows a side view of the electrophoretic apparatus shown in FIGS. 11 and 12 as seen from the left, with some parts removed and shown in phantom.

In order to shut the entrance and exit windows 12f and 12h during the period of electrophoresis, a pair of shutter members 262 and 264 are slidably mounted on the left and right side walls 12e and 12g of the main body 12. The shutter member 262 is connected to a disk 266 fixed to the left end of the operating rod 112 through a connecting lever 268 as shown especially in FIG. 13. Since the lower end of the connecting lever 268 is connected to the disk 266 at the eccentric position thereof, the shutter member 262 is vertically moved so as to open and shut the entrance window 12f as the disk 266 rotates i.e. as the operating rod 112 rotates. The shutter member 264 is connected to another disk 270 fixed to the right end of the operating rod 112 through another connecting lever 272. Since this arrangement of the shutter member 264, the disk 270 and the connecting lever 272 is the same as that of the shutter member 262, the disk 266 and the connecting lever 268, it is apparent that the shutter member 264 is vertically moved so as to open and shut the exit window 12h as the disk rotates i.e. as the operating rod 112 rotates.

In operation, a pair of the boards 210 and 212 are in their lowermost positions shown in FIGS. 11 and 12 by rotating the cam disks 116 and 118 by means of the electric motor 238 and both windows 12f and 12h are in the opened state, before the carrier body 50 is introduced into the main body 12 of the electrophoretic apparatus 500. As shown in FIG. 12, the upper surfaces of the high absorbent paper 108 and 110 attached on the slant surfaces of the 210 and 212 are in the positions below a plane including the upper surfaces of the upper strands of the endless belts 38 and 40 when the boards 210 and 212 are in their lowermost positions. Therefore, the carrier body 50 introduced in the main body 12 is advanced in the rightward direction in FIG. 11 by the endless belts being driven by the motor 44 and is set in place in the same manner as in the cases of the embodiments described hereinbefore with its both side end portions extending outwardly from both endless belts 38 and 40. Then the motor 238 (FIG. 11) is rotated so as to push up the boards 210 and 212 through the cam disks 116 and 118, the vertically movable rods 218 and 220 and the connecting bars 214 and 216. When the cam disks 116 and 118 are rotated at 180° from the positions shown in FIGS. 11 and 12, the boards 210 and 212 push up each side end portions of the carrier body 50 together with the pressing boards 244 and 250. That is, both side end portions of the carrier body 50 are nipped between the pressing boards 244 and 250 and the boards 210 and 212 by the dead loads of the pressing boards 244 and 250 at the position above the upper strands of the endless belts 38 and 40. At the same time the boards 210 and 212 are brought into their uppermost positions, the entrance and exit windows 12f and 12h are closed with the shutter members 262 and 264 since the disks 266 and 270 are simultaneously rotated together with the cam disks 116 and 118. Direct voltage is then applied for the predetermined periods of time through the buffer solution in the buffer solution troughs 22 and 24 and the high absorbent paper 108 and 110 to the carrier body 50 i.e. blood serum applied thereto. After the completion of the electrophoresis for the blood serum applied to the carrier body 50, the boards 210 and 212 are returned to their lowermost positions by the operation of the cam disks 116 and 118 and the carrier body 50 is fed out from the opened exit window 12h by the endless belts 38 and 40. Even though the both side end portions of the carrier body 50 are adhered to the lower surfaces of the pressing boards 244 and 250 due to the viscosity of the buffer solution contained in the carrier body 50 when the boards 210 and 212 returns from their uppermost positions to their lowermost positions, the carrier body 50 is torn off from the lower surfaces of the pressing boards 244 and 250 by the wires 202 and 206 extending above and along the upper strands of the endless belts 38 and 40.

In this fourth embodiment of the present invention, since the endless belts 38 and 40 are disengaged from the carrier body 50 and the entrance and exit windows are closed tightly during the period of time of the electrophoresis so that the ionic density in the main body is maintained at the predetermined value at least during the period of time of the electrophoresis, more precise, correct and favourable analysis of the blood serum may be possible. Furthermore, since the pressing boards 244 and 250 and the boards 210 and 212 are easily taken away from the main body 12 by only lifting them upwardly, the cleaning of the main body 12 or the exchange of the buffer solution 111 may be conveniently performed in this electrophoretic apparatus 500.

What we claim is:

1. An electrophoretic apparatus for use in an analysis of a specimen such as blood serum applied to a belt-like carrier body comprising:

a main body having a chamber portion and entrance and exit windows formed in the opposite portions of the chamber portion, a pair of buffer solution troughs disposed in the chamber portion and respectively containing a buffer solution, a transport means for transporting the carrier body from the entrance window into the chamber portion and out of the chamber portion from the exit window, a pair of high absorbent papers at least a part of each one of which is dipped into the buffer solution in respective buffer solution troughs, a pair of contacting means movably disposed in the chamber portion for contacting each side end portion of the carrier body placed in the chamber portion with respective ones of said pair of high absorbent papers, including an operating rod rotatably mounted on said main body, at least a pair of cam disks mounted on said rod for rotation therewith, a pair of arms each engaging a cam surface of a cam disk for movement as said disk is rotated, and a pair of pressing plates each mounted on one of said arms for pressing said carrier body into contact with one of said papers, wherein direct voltage is applied across both side end portions of the carrier body through the buffer solution in each buffer solution trough and respective high absorbent paper.

2. An apparatus as in claim 1, wherein each of said pressing plates has a flat surface extending parallel to the paper it contacts and wherein said arms extend substantially horizontal and wherein said contacting means further includes vertical rods connecting said plates to said arms.

3. An apparatus as in claim 2, wherein said transport means includes first and second endless belts for engaging said carrier and means for driving said belt and further including further pressing plates for engaging said belts and further vertical rods connecting said further plates to said horizontal arms.

4. An apparatus as in claim 2, further including a pair of wires mounted adjacent to said pressing plates for disengaging said carrier body from said pressing plates when said pressing plates are moved out of contact with said carrier body.

5. An apparatus as in claim 1, wherein said pressing plates are mounted below said carrier and wherein said contacting means includes vertically movable rods and connecting bars connecting said pressing plates to said rigid arms.

6. An apparatus as in claim 5 further including wires mounted adjacent said pressing plates for disengaging said body from said plates when said plates are moved out of contact with said carrier body.

7. An apparatus as in claim 5, further including shutter members for opening and closing said entrance and exit windows and means connecting said operating rod to said shutter means for closing said windows when said pressing plates contact said papers.

8. An electrophoretic apparatus for use in an analysis of a specimen such as blood serum applied to a belt-like carrier body comprising:

a main body having a chamber portion and entrance and exit windows formed in the opposite portions of the chamber portion, a pair of buffer solution troughs disposed in the chamber portion and respectively containing a buffer solution, a transport means for transporting the carrier body from the entrance window into the chamber portion and out of the chamber portion from the exit window, a pair of high absorbent papers at least a part of each one of which is dipped into the buffer solution in respective buffer solution troughs, a pair of contacting means movably disposed in the chamber portion for contacting each side end portion of the carrier body placed in the chamber portion with respective ones of said pair of high absorbent papers including a pair of bar-like pressing members, rotatably mounted on said main housing and having sector shaped cross-sections, an operating rod rotatably mounted on said main body, and means connecting said operating rod to said pressing members for rotating said pressing members to engage said carrier body and press said body into contact with said papers, wherein direct voltage is applied across both side end portions of the carrier body through the buffer solution in each buffer solution trough and respective high absorbent paper.

9. An apparatus as in claim 8, wherein said rotating means includes a pulley and a first and second belt connecting said pulley to said pressing members.

* * * * *